(12) United States Patent
Tang et al.

(10) Patent No.: US 10,240,145 B2
(45) Date of Patent: Mar. 26, 2019

(54) CRISPR/CAS-MEDIATED GENOME EDITING TO TREAT EGFR-MUTANT LUNG CANCER

(71) Applicant: The Board of Trustees of the Leland Stanford Junior University, Stanford, CA (US)

(72) Inventors: Huibin Tang, Palo Alto, CA (US); Joseph B. Shrager, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 6 days.

(21) Appl. No.: 15/360,627

(22) Filed: Nov. 23, 2016

(65) Prior Publication Data

US 2017/0145405 A1 May 25, 2017

Related U.S. Application Data

(60) Provisional application No. 62/260,121, filed on Nov. 25, 2015, provisional application No. 62/263,500, filed on Dec. 4, 2015.

(51) Int. Cl.
| | |
|---|---|
| *C12N 15/10* | (2006.01) |
| *C12N 9/22* | (2006.01) |
| *A61K 38/46* | (2006.01) |
| *A61K 47/54* | (2017.01) |

(52) U.S. Cl.
CPC .......... *C12N 15/102* (2013.01); *A61K 38/465* (2013.01); *A61K 47/549* (2017.08); *C12N 9/22* (2013.01)

(58) Field of Classification Search
CPC .......... C12N 15/102; C12N 9/22; C12N 15/85
See application file for complete search history.

(56) References Cited

U.S. PATENT DOCUMENTS

2017/0334968 A1* 11/2017 Cooper .............. C07K 14/7051

FOREIGN PATENT DOCUMENTS

WO WO-2014089290 A1 * 6/2014 ............... C12N 9/22

* cited by examiner

*Primary Examiner* — Antonio Galisteo Gonzalez
(74) *Attorney, Agent, or Firm* — Knobbe, Martens Olson & Bear, LLP

(57) ABSTRACT

The invention relates to a clustered regularly interspaced short palindromic repeats (CRISPR)/Cas guide RNA (gRNA) comprising a targeting domain that is complementary to human genomic Epidermal Growth Factor Receptor (EGFR) DNA, and a vector system including one or more packaged vector(s) including: (a) a first regulatory element operably linked to a gRNA, and (b) a second regulatory element operably linked to a nucleic acid encoding a Cas protein. Also disclosed are methods of altering a nucleic acid sequence encoding EGFR in a cell including contacting the cell with a vector system, methods of treating lung cancer, and methods of selectively inducing apoptosis in a cell including administering a gRNA to the cell.

14 Claims, 10 Drawing Sheets

Specification includes a Sequence Listing.

```
MRPSGTAGAA  LLALLAALCP  ASRALEEKKV  CQGTSNKLTQ  LGTFEDHFLS   50
LQRMFNNCEV  VLGNLEITYV  QRNYDLSFLK  TIQEVAGYVL  IALNTVERIP  100
LENLQIIRGN  MYENSYALA   VLSNYDANKT  GLKELPMRNL  QEILHGAVRF  150
SNNPALCNVE  SIQWRDIVSS  DFLSNMSMDF  QNHLGSCQKC  DPSCPNGSCW  200
GAGEENCQKL  TKIICAQQCS  GRCRGKSPSD  CCHNQCAAGC  TGPRESDCLV  250
CRKFRDEATC  KDTCPPLMLY  NPTTYQMDVN  PEGKYSFGAT  CVKKCPRNYV  300
VTDHGSCVRA  CGADSYEMEE  DGVRKCKKCE  GPCRKVCNGI  GIGEFKDSLS  350
INATNIKHFK  NCTSISGDLH  ILPVAFRGDS  FTHTPLDPQ   ELDILKTVKE  400
ITGFLLIQAW  PENRTDLHAF  ENLEIIRGRT  KQHGQFSLAV  VSLNITSLGL  450
RSLKEISDGD  VIISGNKNLC  YANTINWKKL  FGTSGQKTKI  ISNRGENSCK  500
ATGQVCHALC  SPEGCWGPEP  RDCVSCRNVS  RGRECVDKCN  LLEGEPREFV  550
ENSECIQCHP  ECLPQAMNIT  CTGRGPDNCI  QCAHYIDGPH  CVKTCPAGVM  600
GENNTLVWKY  ADAGHVCHLC  HPNCTYGCTG  PGLEGCPTNG  PKIPSIATGM  650
VGALLLLVV   ALGIGLFMRR  RHIVRKRTLR  RLLQERELVE  PLTPSGEAPN  700
QALLRILKET  EFKKIKVLGS  GAFGTVYKGL  WIPEGEKVKI  PVAIKELREA  750
TSPKANKEIL  DEAYVMASVD  NPHVCRLLGI  CLTSTVQLIT  QLMPFGCLLD  800
YVREHKDNIG  SQYLLNWCVQ  IAKGMNYLED  RRLVHRDLAA  RNVLVKTPQH  850
VKITDFGLAK  LLGAEEKEYH  AEGGKVPIKW  MALESILHRI  YTHQSDVWSY  900
GVTVWELMTF  GSKPYDGIPA  SEISSILEKG  ERLPQPPICT  IDVYMIMVKC  950
WMIDADSRPK  FRELIIEFSK  MARDPQRYLV  IQGDERMHLP  SPTDSNFYRA  1000
LMDEEDMDDV  VDADEYLIPQ  QGFFSSPSTS  RTPLLSSLSA  TSNNSTVACI  1050
DRNGLQSCPI  KEDSFLQRYS  SDPTGALIED  SIDDTFLPVP  EYINQSVPKR  1100
PAGSVQNPVY  HNQPLNPAPS  RDPHYQDPHS  TAVGNPEYLN  TVQPTCVNST  1150
FDSPAHWAQK  GSHQISLDNP  DYQQDFFPKE  AKPNGIFKGS  TAENAEYLRV  1200
APQSSEFIGA                                                 1210
```

Fig. 2

CRISPR/CAS-MEDIATED GENOME EDITING TO TREAT EGFR-MUTANT LUNG CANCER

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 24953792_1.TXT the date of creation of the ASCII text file is Jan. 5, 2017, and the size of the ASCII text file is 17.6 KB.

FIELD OF THE INVENTION

The invention relates to Clustered Regularly Interspaced Short Palindromic Repeats (CRISPR)/Cas methods and components for editing the human Epidermal Growth Factor Receptor (EGFR) gene and treatment of lung cancer.

DESCRIPTION OF THE RELATED ART

Lung cancer (LCa) is the most common type of cancer among men globally, and it is the leading cancer-related cause of death of both men and women. In 2015, ~150,000 Americans are expected to die from this disease (American Cancer Society (2015) Cancer Facts and Figures 2015. Atlanta: American Cancer Society). Approximately 85% of lung cancers are the non-small-cell type (NSCLC), including adenocarcinomas and squamous cell carcinomas. Accepted LCa treatments, depending upon stage, may include surgery, radiation therapy, and/or targeted/chemotherapy. The non-specific cytotoxicity of chemotherapy has been a long-standing hurdle for the otherwise appealing approach of using drugs to manage cancer. However, the emergence of "targeted" drug therapy with TKIs in EGFR-mutant lung adenocarcinoma has substantially mitigated this concern.

The EGFR is a membrane glycoprotein with an extracellular ligand-binding domain, a transmembrane domain, and an intracellular tyrosine kinase domain. Ligand binding activates the intracellular tyrosine kinase, which via cascading downstream signals promotes a number of intracellular pathways that support the cancer phenotype. These include pathways underlying cellular proliferation, neovascularization, invasion and metastasis, reduced apoptosis, and activation of the Warburg effect (preferred use of aerobic glycolysis as a source of energy). Constitutive activation of the EGFR tyrosine kinase as a result of genetic mutations within it was first reported in a subgroup of lung adenocarcinoma patients (Lynch T J et al (2004) "Activating mutations in the epidermal growth factor receptor underlying responsiveness of non-small-cell lung cancer to gefitinib" *N Engl J Med* 350: 2129-2139; Paez J G et al (2004) "EGFR mutations in lung cancer: correlation with clinical response to gefitinib therapy" *Science* 304: 1497-1500). These EGFR mutations are more frequent in female patients of East Asian ancestry. The most common mutations are deletions in exon 19 (del-E746-A750, ~50% of patients), and a point mutation in exon 21 (~40%) that substitutes leucine with arginine at codon 858 (L858R). Several drugs, such as gefitinib and erlotinib, have been developed that inhibit the tyrosine kinase activity of EGFR by competing with ATP for the ATP-binding pocket in EGFR's tyrosine kinase domain. These drugs (TKIs) have become first-line therapy in metastatic EGFR-mutant NSCLC.

Although TKIs have proven to have remarkable initial efficacy in EGFR-mutant LCa, nearly all patients unfortunately ultimately develop acquired resistance to the drugs within 2 years. This acquired drug resistance often results from a secondary mutation at position 790 in exon 20 (T790M, substituting threonine with methionine; found in ~65% of tumors with acquired resistance to TKIs). T790M-related drug resistance may result from alteration of inhibitor binding in the ATP pocket of EGFR and restored binding affinity for ATP. To overcome drug resistance, several second-generation drugs (afatinib/gilotrif, dacomitinib, neratinib) and third-generation drugs (CO-1686, AZD9291), have been developed. The second-generation drugs are irreversible inhibitors, while the third-generation drugs are selective to the T790M mutation. While the clinical effectiveness of these drugs has not yet been completely elucidated, preliminary data indicates that they may add about 9-13 months of progression-free survival in appropriate patients (Cross D A et al (2014) "AZD9291, an irreversible EGFR TKI, overcomes T790M-mediated resistance to EGFR inhibitors in lung cancer" *Cancer Discov* 4: 1046-1061; Politi K et al. (2015) "The Next Wave of EGFR Tyrosine Kinase Inhibitors Enter the Clinic" *Cancer Cell* 27: 751-753).

Not surprisingly, we are now learning of resistance mutations (e.g., C797S) induced by third-generation TKIs (Politi K et al. (2015) "The Next Wave of EGFR Tyrosine Kinase Inhibitors Enter the Clinic" *Cancer Cell* 27: 751-753; Thress K S et al (2015) "Acquired EGFR C797S mutation mediates resistance to AZD9291 in non-small cell lung cancer harboring EGFR T790M" *Nat Med* 21: 560-562). Rather than continuing to repeat this cycle of inducing new resistance mutations via the selective pressure created by additional targeted drug therapies, the development of entirely novel approaches seems appropriate.

CRISPR/Cas9 is an RNA-guided gene-editing tool that uses a bacterially derived endonuclease Cas9 (or its mutant nickase) and a single guide RNA (sgRNA) to introduce a double (or single)-strand break at a specific location within the genome by matching the sequences between sgRNA and genomic DNA. The subsequent DNA repair then introduces an insertion or causes a deletion in the target gene through either homology-directed repair (HDR) or non-homologous end-joining (NHEJ) (Cong et al, 2013). CRISPR/Cas-mediated gene knockout would be expected to be more efficient than RNA interference-mediated gene knockdown, and has until now provided a convenient laboratory tool to study gene function (Chen S et al (2015) "Genome-wide CRISPR screen in a mouse model of tumor growth and metastasis" *Cell* 160: 1246-1260). More importantly, it makes it theoretically possible to repair genetic mutations in clinical diseases (Ebina H et al. (2013) "Harnessing the CRISPR/Cas9 system to disrupt latent HIV-1 provirus" *Sci Rep* 3: 2510; Sánchez-Rivera F J and Jacks T (2015) "Applications of the CRISPR-Cas9 system in cancer biology" *Nat Rev Cancer* 7: 387-395).

SUMMARY OF THE INVENTION

Some embodiments relate to a clustered regularly interspaced short palindromic repeats (CRISPR)/Cas guide RNA (gRNA) comprising a targeting domain that is complementary to human genomic Epidermal Growth Factor Receptor (EGFR) DNA.

In some embodiments, the gRNA further comprises:
a first complementarity domain;
a linking domain;
a second complementarity domain, which is complementary to the first complementarity domain;

a proximal domain; and optionally, a tail domain.

In some embodiments, the gRNA is configured to restore a wild type sequence in the human genomic EGFR DNA.

In some embodiments, the gRNA is configured to introduce a frameshift mutation or a stop codon into the human genomic EGFR DNA.

In some embodiments, the targeting domain is complementary to a region of genomic DNA encoding human EGFR selected from the group consisting of exon 19, exon 20 and exon 21.

In some embodiments, the targeting domain is complementary to exon 19 of genomic DNA encoding human EGFR and wherein the targeting domain is configured to restore a wild type sequence at E746-A750 or to introduce a frameshift mutation or a stop codon in exon 19.

In some embodiments, the gRNA comprises a sequence selected from the group consisting of SEQ ID NO: 4, SEQ ID NO: 6, SEQ ID NO: 8, SEQ ID NO: 10, SEQ ID NO: 12 and SEQ ID NO: 14.

In some embodiments, the targeting domain is complementary to exon 20 of genomic DNA encoding human EGFR and wherein the targeting domain is configured to introduce a frameshift mutation or a stop codon in exon 20.

In some embodiments, the gRNA comprises a sequence selected from the group consisting of SEQ ID NO: 17, SEQ ID NO: 19, SEQ ID NO: 21, SEQ ID NO: 23, and SEQ ID NO: 25.

In some embodiments, the targeting domain is complementary to exon 21 of genomic DNA encoding human EGFR and wherein the targeting domain is configured to restore a leucine residue at position 858 or to introduce a frameshift mutation or a stop codon in exon 21.

In some embodiments, the gRNA comprises a sequence selected from the group consisting of SEQ ID NO: 28, SEQ ID NO: 30, SEQ ID NO: 32, SEQ ID NO: 34, SEQ ID NO: 36, SEQ ID NO: 38 and SEQ ID NO: 40.

Some embodiments relate to a vector system comprising one or more packaged vector(s) comprising:

(a) a first regulatory element operably linked to a sequence encoding a gRNA as disclosed herein, and (b) a second regulatory element operably linked to a nucleic acid encoding a Cas protein.

In some embodiments of vector system, the Cas protein is a Cas9 protein.

In some embodiments of vector system, the Cas9 protein is selected from the group consisting of *Streptococcus pyogenes* Cas9, *Streptococcus thermophilus* Cas9, *Staphylococcus aureus* Cas9 and *Neisseria meningitides* Cas9.

In some embodiments of vector system, said one or more packaged vectors is/are selected from the group consisting of retroviruses, lentiviruses, adenovirus, adeno-associated virus (AAV), vaccinia viruses, poxviruses, and herpes simplex viruses.

Some embodiments of vector system comprise only a single packaged vector.

Some embodiments relate to a method of altering a nucleic acid sequence encoding EGFR in a cell comprising contacting said cell with a vector system according to claim 12.

Some embodiments relate to a method of treating lung cancer in a subject comprising administering a vector system, as disclose herein, to said subject.

In some embodiments, the lung cancer is a non-small cell lung cancer (NSCLC).

Some embodiments relate to a method of selectively inducing apoptosis in a cell comprising administering a gRNA, as disclose herein, to the cell.

BRIEF DESCRIPTION OF THE DRAWINGS

FIG. 2. Amino acid sequence of human EGFR (SEQ ID NO: 1)

DETAILED DESCRIPTION OF THE PREFERRED EMBODIMENT

Figure 1:
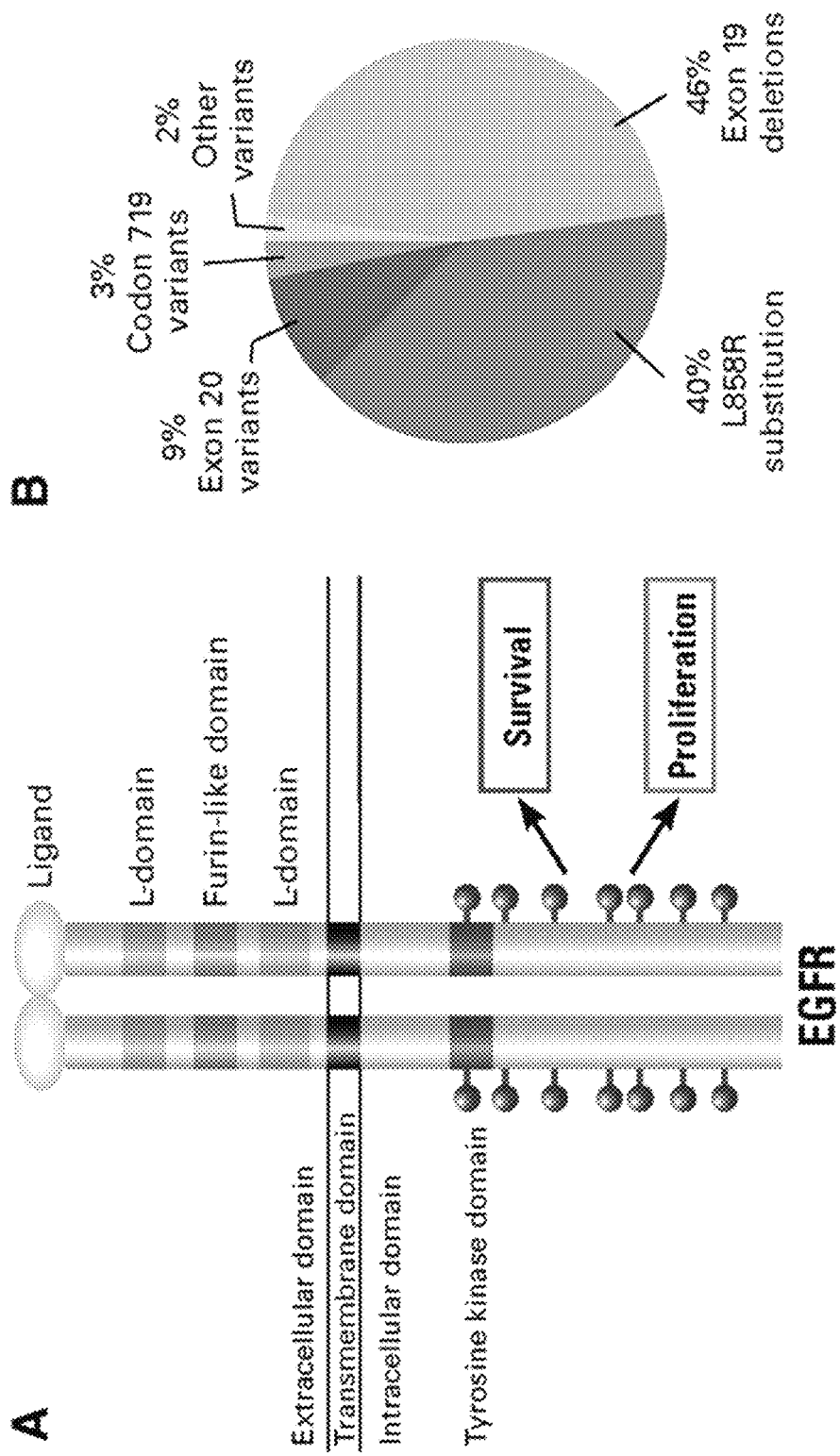
FIG. 1. (A) Diagram of the transmembrane topology of the epidermal growth factor receptor (EGFR), including an extracellular domain, a transmembrane domain and an intracellular domain that includes a tyrosine kinase domain. (B) EGFR mutations and corresponding incidence of cancer.
Figure 3:
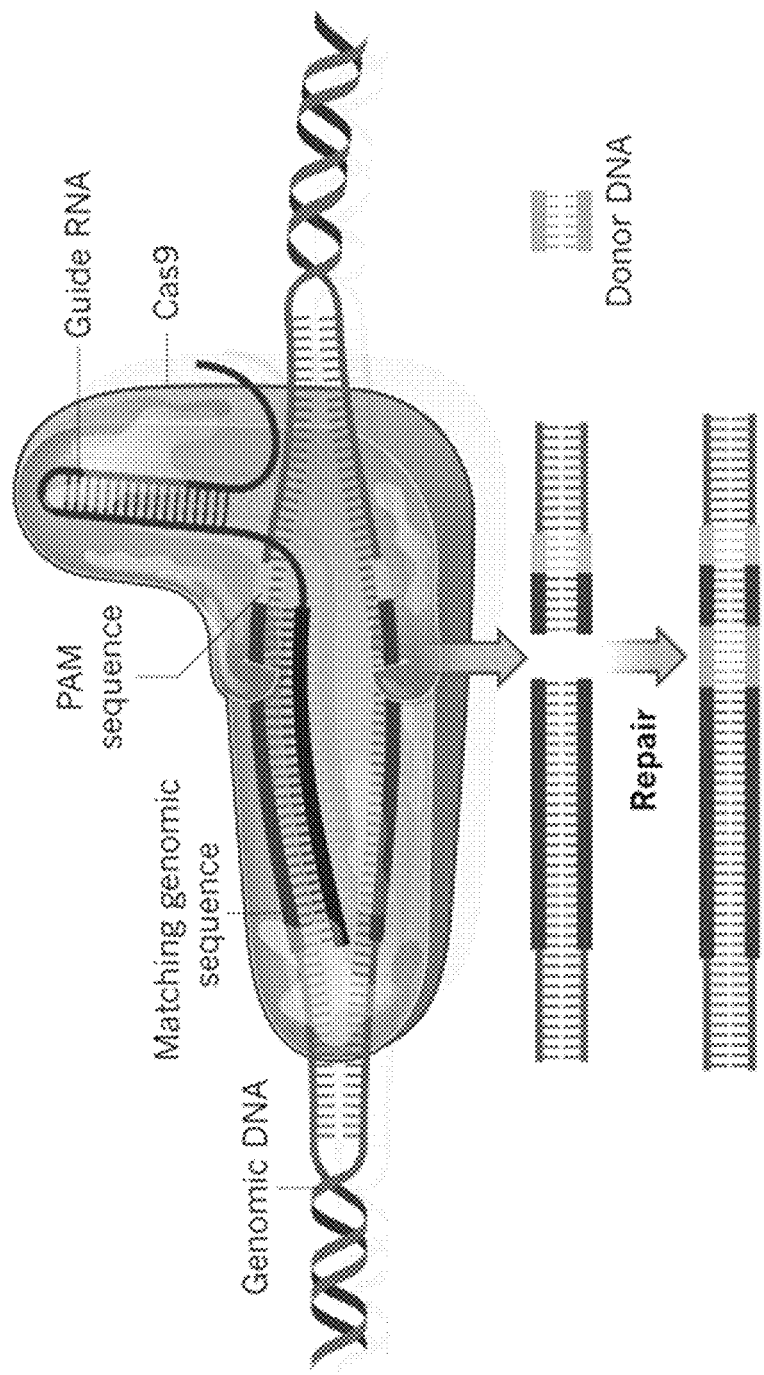
FIG. 3. Schematic diagram of CRISPR/Cas9-mediated genome editing technology.

We disclose a new personalized molecular surgery approach to correct or destroy mutated EGFR using CRISPR/Cas9-mediated genome-editing technology. The *Homo sapiens* epidermal growth factor receptor (EGFR), variant 1, mRNA transcript is catalogued by Genbank as NCBI Reference Sequence NM_005228.4.

A "guide RNA" (gRNA) molecule, as used herein, refers to a nucleic acid that promotes the specific targeting or homing of a gRNA molecule/Cas9 molecule complex to a target nucleic acid. gRNA molecules can be unimolecular (having a single RNA molecule), sometimes referred to herein as "chimeric" gRNAs, or modular (comprising more than one, and typically two, separate RNA molecules). gRNA are a synthetic fusion of the endogenous bacterial crRNA and tracrRNA. gRNA provide both targeting specificity and scaffolding/binding ability for Cas9 nuclease. They do not exist in nature. gRNA are sometimes referred to as "single guide RNA" or "sgRNA". A gRNA molecule comprises a number of domains, which are described in more detail below.

Some embodiments relate to a unimolecular, or chimeric, guide RNA (gRNA) comprises, preferably from 5' to 3':

a targeting domain (which is complementary to a target nucleic acid);
a first complementarity domain;
a linking domain;
a second complementarity domain (which is complementary to the first complementarity domain);
a proximal domain; and
optionally, a tail domain.

The targeting domain comprises a nucleotide sequence that is complementary, e.g., at least 80, 85, 90, or 95% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In an embodiment, the target domain itself comprises, in the 5' to 3' direction, an optional secondary domain, and a core domain. In an embodiment, the core domain is fully complementary with the target sequence. In an embodiment, the targeting domain is 5 to 50, 10 to 40, e.g., 10 to 30, e.g., 15 to 30, e.g., 15 to 25 nucleotides in length. In an embodiment, the targeting domain is 15, 16, 17, 18, 19, 20, 21, 22, 23, 24 or 25 nucleotides in length. The strand of the target nucleic acid with which the targeting domain is complementary is referred to herein as the complementary strand. Some or all of the nucleotides of the domain can have a modification.

The first complementarity domain is complementary with the second complementarity domain, and in an embodiment, has sufficient complementarity to the second complementarity domain to form a duplexed region under at least some physiological conditions. In an embodiment, the first complementarity domain is 5 to 30 nucleotides in length. In an embodiment, the first complementarity domain is 5 to 25 nucleotides in length. In an embodiment, the first complementary domain is 7 to 25 nucleotides in length. In an embodiment, the first complementary domain is 7 to 22 nucleotides in length. In an embodiment, the first complementary domain is 7 to 18 nucleotides in length. In an embodiment, the first complementary domain is 7 to 15 nucleotides in length. In an embodiment, the first complementary domain is 5, 6, 7, 8, 9, 10, 11, 12, 13, 14, 15, 16, 17, 18, 19, 20, 21, 22, 23, 24, or 25 nucleotides in length.

In an embodiment, the first complementary domain comprises 3 subdomains, which, in the 5' to 3' direction are: a 5' subdomain, a central subdomain, and a 3' subdomain. In an embodiment, the 5' subdomain is 4-9, e.g., 4, 5, 6, 7, 8 or 9 nucleotides in length. In an embodiment, the central subdomain is 1, 2, or 3, e.g., 1, nucleotide in length. In an embodiment, the 3' subdomain is 3 to 25, e.g., 4-22, 4-18, or 4 to 10, or 3, 4, 5, 6, 7, 8, 9, 10, 11, 12, 13, 14, 15, 16, 17, 18, 19, 20, 21, 22, 23, 24, or 25, nucleotides in length.

The first complementarity domain can share homology with, or be derived from, a naturally occurring first complementarity domain. In an embodiment, it has at least 50% homology with a first complementarity domain disclosed herein, e.g., a *Streptococcus pyogenes* (*S. pyogenes*) or *Streptococcus thermophiles* (*S. thermophiles*), first complementarity domain.

A linking domain serves to link the first complementarity domain with the second complementarity domain of a unimolecular gRNA. The linking domain can link the first and second complementarity domains covalently or non-covalently. In an embodiment, the linkage is covalent. In an embodiment, the linking domain covalently couples the first and second complementarity domains. In an embodiment, the linking domain is, or comprises, a covalent bond interposed between the first complementarity domain and the second complementarity domain. Typically, the linking domain comprises one or more, e.g., 2, 3, 4, 5, 6, 7, 8, 9, or 10 nucleotides.

In modular gRNA molecules the two molecules can be associated by virtue of the hybridization of the complementarity domains.

A wide variety of linking domains are suitable for use in unimolecular gRNA molecules. Linking domains can consist of a covalent bond, or be as short as one or a few nucleotides, e.g., 1, 2, 3, 4, or 5 nucleotides in length.

In an embodiment, a linking domain is 2, 3, 4, 5, 6, 7, 8, 9, 10, 15, 20, or 25 or more nucleotides in length. In an embodiment, a linking domain is 2 to 50, 2 to 40, 2 to 30, 2 to 20, 2 to 10, or 2 to 5 nucleotides in length. In an embodiment, a linking domain shares homology with, or is derived from, a naturally occurring sequence, e.g., the sequence of a tracrRNA that is 5' to the second complementarity domain. In an embodiment, the linking domain has at least 50% homology with a linking domain disclosed herein.

In an embodiment, a modular gRNA can comprise additional sequence, 5' to the second complementarity domain, referred to herein as the 5' extension domain. In an embodiment, the 5' extension domain is, 2-10, 2-9, 2-8, 2-7, 2-6, 2-5, 2-4 nucleotides in length. In an embodiment, the 5' extension domain is 2, 3, 4, 5, 6, 7, 8, 9, or 10 or more nucleotides in length.

The second complementarity domain is complementary with the first complementarity domain, and in an embodiment, has sufficient complementarity to the second complementarity domain to form a duplexed region under at least some physiological conditions. In an embodiment, the second complementarity domain can include sequence that lacks complementarity with the first complementarity domain, e.g., sequence that loops out from the duplexed region.

In an embodiment, the second complementarity domain is 5 to 27 nucleotides in length. In an embodiment, it is longer than the first complementarity region.

In an embodiment, the second complementarity domain is 7 to 27 nucleotides in length. In an embodiment, the second complementary domain is 7 to 25 nucleotides in length. In an embodiment, the second complementary domain is 7 to 20 nucleotides in length. In an embodiment, the second complementary domain is 7 to 17 nucleotides in length. In an embodiment, the complementary domain is 5, 6, 7, 8, 9, 10, 11, 12, 13, 14, 15, 16, 17, 18, 19, 20, 21, 22, 23, 24 or 25 nucleotides in length.

In an embodiment, the second complementarity domain comprises 3 subdomains, which, in the 5' to 3' direction are: a 5' subdomain, a central subdomain, and a 3' subdomain. In an embodiment, the 5' subdomain is 3 to 25, e.g., 4 to 22, 4 to 18, or 4 to 10, or 3, 4, 5, 6, 7, 8, 9, 10, 11, 12, 13, 14, 15, 16, 17, 18, 19, 20, 21, 22, 23, 24, or 25 nucleotides in length. In an embodiment, the central subdomain is 1, 2, 3, 4 or 5, e.g., 3, nucleotides in length. In an embodiment, the 3' subdomain is 4 to 9, e.g., 4, 5, 6, 7, 8 or 9 nucleotides in length.

In an embodiment, the 5' subdomain and the 3' subdomain of the first complementarity domain, are respectively, complementary, e.g., fully complementary, with the 3' subdomain and the 5' subdomain of the second complementarity domain.

The second complementarity domain can share homology with or be derived from a naturally occurring second complementarity domain. In an embodiment, it has at least 50% homology with a second complementarity domain disclosed herein, e.g., an *S. pyogenes*, or *S. thermophilus*, first complementarity domain.

Some or all of the nucleotides of the domain can have a modification.

In an embodiment, the proximal domain is 5 to 20 nucleotides in length. In an embodiment, the proximal domain can share homology with or be derived from a naturally occurring proximal domain. In an embodiment, it has at least 50% homology with a proximal domain disclosed herein, e.g., an *S. pyogenes*, or *S. thermophilus*, proximal domain.

A broad spectrum of tail domains are suitable for use in gRNA molecules. In an embodiment, the tail domain is 0 (absent), 1, 2, 3, 4, 5, 6, 7, 8, 9, or 10 nucleotides in length. In an embodiment, the tail domain nucleotides are from or share homology with sequence from the 5' end of a naturally occurring tail domain. In an embodiment, the tail domain includes sequences that are complementary to each other and which, under at least some physiological conditions, form a duplexed region.

In an embodiment, the tail domain is absent or is 1 to 50 nucleotides in length. In an embodiment, the tail domain can share homology with or be derived from a naturally occurring proximal tail domain. In an embodiment, it has at least 50% homology with a tail domain disclosed herein, e.g., an *S. pyogenes*, or *S. thermophilus*, tail domain.

In an embodiment, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When alternate pol-III promoters are used, these nucleotides may be various numbers or uracil bases or may include alternate bases.

The "targeting domain" of the gRNA is complementary to the "target domain" on the target nucleic acid. The strand of the target nucleic acid comprising the nucleotide sequence complementary to the core domain of the gRNA is referred to herein as the "complementary strand" of the target nucleic acid. Guidance on the selection of targeting domains can be found, e.g., in Fu Y et al., NAT BIOTECHNOL 2014 (doi: 10.1038/nbt.2808) and Sternberg S H et al., NATURE 2014 (doi: 10.1038/nature13011).

Methods for Designing gRNAs

Methods for selection and validation of target sequences as well as off-target analyses are described, e.g., in. Mali et al., 2013 SCIENCE 339(6121): 823-826; Hsu et al., 2013 NAT BIOTECHNOL, 31(9): 827-32; Fu et al., 2014 NAT BIOTECHNOL, doi: 10.1038/nbt.2808. PubMed PMID: 24463574; Heigwer et al., 2014 NAT METHODS 11(2): 122-3. doi: 10.1038/nmeth.2812. PubMed PMID: 24481216; Bae et al., 2014 BIOINFORMATICS PubMed PMID: 24463181; Xiao A et al., 2014 BIOINFORMATICS PubMed PMID: 24389662.

For example, a software tool can be used to optimize the choice of sgRNA within a user's target sequence, e.g., to minimize total off-target activity across the genome. Off target activity may be other than cleavage. For each possible gRNA choice e.g., using *S. pyogenes* Cas9, the tool can identify all off-target sequences (e.g., preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods.

Cas9 Molecules

Cas9 molecules of a variety of species can be used in the methods and compositions described herein. While the *S. pyogenes* and *S. thermophilus* Cas9 molecules are typically used, Cas9 molecules of, derived from, or based on the Cas9 proteins of other species can be used, e.g., *Staphylococcus aureus, Neisseria meningitides*.

A Cas9 molecule, as that term is used herein, refers to a molecule that can interact with a sgRNA molecule and, in concert with the sgRNA molecule, localize (e.g., target or home) to a site which comprises a target domain and PAM sequence.

In an embodiment, the Cas9 molecule is capable of cleaving a target nucleic acid molecule. A Cas9 molecule that is capable of cleaving a target nucleic acid molecule is referred to herein as an eaCas9 (an enzymatically active Cas9) molecule. In an embodiment, an eaCas9 molecule, comprises one or more of the following activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in an embodiment is the presence of two nickase activities;

an endonuclease activity;

an exonuclease activity; and a helicase activity, i.e., the ability to unwind the helical structure of a double stranded nucleic acid.

In an embodiment, an enzymatically active Cas9 or an eaCas9 molecule cleaves both DNA strands and results in a double stranded break. In an embodiment, an eaCas9 molecule cleaves only one strand, e.g., the strand to which the gRNA hybridizes to, or the strand complementary to the strand the gRNA hybridizes with. In an embodiment, an eaCas9 molecule comprises cleavage activity associated with an HNH-like domain. In an embodiment, an eaCas9 molecule comprises cleavage activity associated with an N-terminal RuvC-like domain. In an embodiment, an eaCas9 molecule comprises cleavage activity associated with an HNH-like domain and cleavage activity associated with an N-terminal RuvC-like domain. In an embodiment, an eaCas9 molecule comprises an active, or cleavage competent, HNH-like domain and an inactive, or cleavage incompetent, N-terminal RuvC-like domain. In an embodiment, an eaCas9 molecule comprises an inactive, or cleavage incompetent, HNH-like domain and an active, or cleavage competent, N-terminal RuvC-like domain.

In an embodiment, the ability of an eaCas9 molecule to interact with and cleave a target nucleic acid is PAM sequence dependent. A PAM sequence is a sequence in the target nucleic acid. In an embodiment, cleavage of the target nucleic acid occurs upstream from the PAM sequence. EaCas9 molecules from different bacterial species can recognize different sequence motifs (e.g., PAM sequences). In an embodiment, an eaCas9 molecule of S. pyogenes recognizes the sequence motif NGG and directs cleavage of a target nucleic acid sequence 1 to 10, e.g., 3 to 5, base pairs upstream from that sequence. See, e.g., Mali et al., SCIENCE 2013; 339(6121): 823-826. In an embodiment, an eaCas9 molecule of S. thermophilus recognizes the sequence motif NGGNG and NNAGAAW (W=A or T) and directs cleavage of a core target nucleic acid sequence 1 to 10, e.g., 3 to 5, base pairs upstream from these sequences. See, e.g., Horvath et al., SCIENCE 2010; 327(5962):167-170, and Deveau et al., J BACTERIOL 2008; 190(4): 1390-1400. In an embodiment, an eaCas9 molecule of S. mutans recognizes the sequence motif NGG or NAAR (R=A or G) and directs cleavage of a core target nucleic acid sequence 1 to 10, e.g., 3 to 5 base pairs, upstream from this sequence. See, e.g., Deveau et al., J BACTERIOL 2008; 190(4): 1390-1400. In an embodiment, an eaCas9 molecule of S. aureus recognizes the sequence motif NNGRR (R=A or G) and directs cleavage of a target nucleic acid sequence 1 to 10, e.g., 3 to 5, base pairs upstream from that sequence. In an embodiment, an eaCas9 molecule of N. meningitidis recognizes the sequence motif NNNNGATT and directs cleavage of a target nucleic acid sequence 1 to 10, e.g., 3 to 5, base pairs upstream from that sequence. See, e.g., Hou et al., PNAS EARLY EDITION 2013, 1-6. The ability of a Cas9 molecule to recognize a PAM sequence can be determined, e.g., using a transformation assay described in Jinek et al., SCIENCE 2012, 337:816.

Some Cas9 molecules have the ability to interact with a sgRNA molecule, and in conjunction with the sgRNA molecule home (e.g., targeted or localized) to a core target domain, but are incapable of cleaving the target nucleic acid, or incapable of cleaving at efficient rates. Cas9 molecules having no, or no substantial, cleavage activity are referred to herein as an eiCas9 (an enzymatically inactive Cas9) molecule. For example, an eiCas9 molecule can lack cleavage activity or have substantially less, e.g., less than 20, 10, 5, 1 or 0.1% of the cleavage activity of a reference Cas9 molecule, as measured by an assay described herein.

Exemplary naturally occurring Cas9 molecules are described in Chylinski et al., RNA Biology 2013; 10:5, 727-737.

In an embodiment, a Cas9 molecule comprises an HNH-like domain and an RuvC-like domain. In an embodiment, cleavage activity is dependent on a RuvC-like domain and an HNH-like domain. A Cas9 molecule, e.g., an eaCas9 or eiCas9 molecule, can comprise one or more of the following domains: a RuvC-like domain and an HNH-like domain. In an embodiment, a cas9 molecule is an eaCas9 molecule and the eaCas9 molecule comprises a RuvC-like domain, e.g., a RuvC-like domain described below, and/or an HNH-like domain, e.g., an HNH-like domain described below. In an embodiment, a Cas9 molecule is an eiCas9 molecule comprising one or more difference in an RuvC-like domain and/or in an HNH-like domain as compared to a reference Cas9 molecule, and the eiCas9 molecule does not cleave a nucleic acid, or cleaves with significantly less efficiency than does wildype, e.g., when compared with wild type in a cleavage assay, e.g., as described herein, cuts with less than 50, 25, 10, or 1% of the a reference Cas9 molecule, as measured by an assay described herein.

In an embodiment, a RuvC-like domain cleaves, a single strand, e.g., the non-complementary strand of the target nucleic acid molecule. A Cas9 molecule can include more than one RuvC-like domain (e.g., one, two, three or more RuvC-like domains). In an embodiment, an RuvC-like domain is at least 5, 6, 7, 8 amino acids in length but not more than 20, 19, 18, 17, 16 or 15 amino acids in length. In an embodiment, the cas9 molecule comprises an N-terminal RuvC-like domain of about 10 to 20 amino acids, e.g., about 15 amino acids in length.

Altered Cas9 Molecules

Naturally occurring Cas9 molecules possess a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In an embodiment, a Cas9 molecules can include all or a subset of these properties. In typical embodiments, Cas9 molecules have the ability to interact with a gRNA molecule and, in concert with the gRNA molecule, localize to a site in a nucleic acid. Other activities, e.g., PAM specificity, cleavage activity, or helicase activity can vary more widely in Cas9 molecules.

Cas9 molecules with desired properties can be made in a number of ways, e.g., by alteration of a parental, e.g., naturally occurring Cas9 molecules to provide an altered Cas9 molecule having a desired property. For example, one or more mutations or differences relative to a parental Cas9 molecule can be introduced. Such mutations and differences comprise: substitutions (e.g., conservative substitutions or substitutions of non-essential amino acids); insertions; or deletions. In an embodiment, a Cas9 molecule can comprises one or more mutations or differences, e.g., at least 1, 2, 3, 4, 5, 10, 15, 20, 30, 40 or 50 mutations but less than 200, 100, or 80 mutations relative to a reference Cas9 molecule.

In an embodiment, a mutation or mutations do not have a substantial effect on a Cas9 activity, e.g. a Cas9 activity described herein. In an embodiment, a mutation or mutations have a substantial effect on a Cas9 activity, e.g. a Cas9 activity described herein. In an embodiment, exemplary activities comprise one or more of PAM specificity, cleavage activity, and helicase activity. A mutation(s) can be present, e.g., in: one or more RuvC-like domain, e.g., an N-terminal RuvC-like domain; an HNH-like domain; a region outside the RuvC-like domains and the HNH-like domain. In some embodiments, a mutation(s) is present in an N-terminal RuvC-like domain. In some embodiments, a mutation(s) is present in an HNH-like domain. In some embodiments, mutations are present in both an N-terminal RuvC-like domain and an HNH-like domain.

Whether or not a particular sequence, e.g., a substitution, may affect one or more activity, such as targeting activity, cleavage activity, etc, can be evaluated or predicted, e.g., by evaluating whether the mutation is conservative. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

Cas9 Molecules with Altered PAM Recognition or No PAM Recognition

Naturally occurring Cas9 molecules can recognize specific PAM sequences, for example the PAM recognition sequences for *S. pyogenes, S. thermophilus, S. mutans, S. aureus* and *N. meningitidis*.

In an embodiment, a Cas9 molecule has the same PAM specificities as a naturally occurring Cas9 molecule. In other embodiments, a Cas9 molecule has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule recognizes to decrease off target sites and/or improve specificity; or eliminate a PAM recognition requirement. In an embodiment, a Cas9 molecule can be altered, e.g., to increase length of PAM recognition sequence and/or improve Cas9 specificity to high level of identity to decrease off target sites and increase specificity. In an embodiment, the length of the PAM recognition sequence is at least 4, 5, 6, 7, 8, 9, 10 or 15 amino acids in length. Cas9 molecules that recognize different PAM sequences and/or have reduced off-target activity can be generated using directed evolution.

Non-Cleaving and Modified-Cleavage Cas9 Molecules

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of *S. pyogenes*, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

Modified Cleavage eaCas9 Molecules

In an embodiment, an eaCas9 molecule comprises one or more of the following activities: cleavage activity associated with an N-terminal RuvC-like domain; cleavage activity associated with an HNH-like domain; cleavage activity associated with an HNH domain and cleavage activity associated with an N-terminal RuvC-like domain.

Nucleic Acids Encoding Cas9 Molecules

Exemplary nucleic acids encoding Cas9 molecules are described in Cong et al., SCIENCE 2013, 399(6121):819-823; Wang et al., CELL 2013, 153(4):910-918; Mali et al., SCIENCE 2013, 399(6121):823-826; Jinek et al., SCIENCE 2012, 337(6096):816-821.

Functional Analysis of Candidate Molecules

Candidate Cas9 molecules, candidate sgRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek el al., SCIENCE 2012; 337(6096):816-821.

Binding and Cleavage Assay: Testing the Endonuclease Activity of Cas9 Molecule

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 0.5 units T4 polynucleotide kinase and ~3-6 pmol (~20-40 mCi) [γ-32P]-ATP in 1×T4 polynucleotide kinase reaction buffer at 37° C. for 30 min, in a 50 µL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 µl. Reactions are initiated by the addition of 1 µl target DNA (10 nM) and incubated for 1 h at 37° C. Reactions are quenched by the addition of 20 µl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Binding Assay: Testing the Binding of Cas9 Molecule to Target DNA

Exemplary methods for evaluating the binding of Cas9 molecule to target DNA are described, e.g., in Jinek et al., SCIENCE 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated H$_2$O. Eluted DNA is ethanol precipitated and dissolved in DEPC-treated H$_2$O. DNA samples are 5' end labeled with [γ-$^{32}$P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM MgCl$_2$, 1 mM DTT and 10% glycerol in a total volume of 10 μl. Cas9 protein molecule is programmed with equimolar amounts of pre-annealed gRNA molecule and titrated from 100 pM to 1 μM. Radiolabeled DNA is added to a final concentration of 20 pM. Samples are incubated for 1 h at 37° C. and resolved at 4° C. on an 8% native polyacrylamide gel containing 1×TBE and 5 mM MgCl$_2$. Gels are dried and DNA visualized by phosphorimaging.

HDR Repair

As described herein, nuclease-induced homology directed repair (HDR) can be used to alter a target sequence and correct (e.g., repair or edit) a mutation in the genome. While not wishing to be bound by theory, it is believed that alteration of the target sequence occurs by homology-directed repair (HDR) with a donor template or template nucleic acid. For example, the donor template or the template nucleic acid provides for alteration of the target sequence. It is contemplated that a plasmid donor can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence depends on cleavage by a Cas9 molecule. Cleavage by Cas9 can comprise a double strand break or two single strand breaks.

In an embodiment, a mutation can be corrected by either a single double-strand break or two single strand breaks. In an embodiment, a mutation can be corrected by: (1) a single double-strand break, (2) two single strand breaks, (3) two double stranded breaks with a break occurring on each side of the target sequence, (4) one double stranded breaks and two single strand breaks with the double strand break and two single strand breaks occurring on each side of the target sequence or (5) four single stranded breaks with a pair of single stranded breaks occurring on each side of the target sequence.

Double Strand Break Mediated Correction

In an embodiment, double strand cleavage is effected by a Cas9 molecule-having cleavage activity associated with an HNH-like domain and cleavage activity associated with a RuvC-like domain, e.g., an N-terminal RuvC-like domain, e.g., a wild type Cas9. Such embodiments require only a single gRNA.

Single Strand Break Mediated Correction

In other embodiments, two single strand breaks, or nicks, are effected by a Cas9 molecule having nickase activity, e.g., cleavage activity associated with an HNH-like domain or cleavage activity associated with an N-terminal RuvC-like domain. Such embodiments require two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA).

In an embodiment, in which a nickase and two gRNAs are used to position two single strand nicks, one nick is on the + strand and one nick is on the − strand of the target nucleic acid. The PAMs are outwardly facing. The gRNAs can be selected such that the gRNAs are separated by, from about 0-50, 0-100, or 0-200 nucleotides. In an embodiment, there is no overlap between the target sequence that is complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding.

In an embodiment, a single nick can be used to induce HDR. It is contemplated herein that a single nick can be used to increase the ratio of HR to NHEJ at a given cleavage site.

Placement of the Double Strand Break or a Single Strand Break Relative to Target Position The double strand break or single strand break in one of the strands should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as donor sequence may only be used to correct sequence within the end resection region.

In an embodiment, in which a gRNA (unimolecular (or chimeric) or modular gRNA) and Cas9 nuclease induce a double strand break for the purpose of inducing HDR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In an embodiment, in which two guide RNAs (gRNAs) (independently, unimolecular (or chimeric) or modular gRNA) complexing with Cas9 nickases induce two single strand breaks for the purpose of inducing HDR-mediated correction, the closer nick is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-55 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position (e.g., the first gRNA is used to target upstream (i.e., 5') of the target position and the second gRNA is used to target downstream (i.e., 3') of the target position). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the target position and the second gRNA is used to target downstream (i.e., 3') of the target position). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35, to 50, 40 to 50, 45 to 50, 35 to 45, or 40 to 45 bp) and no more than 100 bp away from each other (e.g., no more than 90, 80, 70, 60, 50, 40, 30, 20 or 10 bp).

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position (e.g., the first gRNA is used to target upstream (i.e., 5') of the mutation in a gene and the second gRNA is used to target downstream (i.e., 3') of the mutation in a gene. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Length of the Homology Arms

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements, e.g., ALU repeats, LINE repeats.

Exemplary homology arm lengths include a least 50, 100, 250, 500, 750 or 1000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the gRNA binds). In an embodiment, a target position is upstream or downstream of a target sequence (e.g., the sequence to which the gRNA binds).

A template nucleic acid, as that term is used herein, refers to a nucleic acid sequence which can be used in conjunction with a Cas9 molecule and a gRNA molecule to alter the structure of a target position. In an embodiment, the target nucleic acid is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified or non-naturally occurring base into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

NHEJ Approaches for Gene Targeting

As described herein, nuclease-induced non-homologous end-joining (NHEJ) can be used to target gene-specific knockouts. Nuclease-induced NHEJ can also be used to remove (e.g., delete) sequence in a gene of interest.

While not wishing to be bound by theory, it is believed that, in an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position (e.g., of a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, VII-25, IX-1, IX-1A, IX-2, IX-3, XIV-1, or Section VIII) to remove the nucleic acid sequence between the two cuts (e.g., the region between the two breaks is deleted). In one embodiment, two gRNAs, e.g., independently, unimolecular (or chimeric) or modular gRNA, are configured to position a double-strand break on both sides of a target position (e.g., the first gRNA is used to target upstream (i.e., 5') of the mutation in a gene or pathway described herein, and the second gRNA is used to target downstream (i.e., 3') of the mutation in a gene or pathway described herein). In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of a target position (e.g., the first gRNA is used to target upstream (i.e., 5') of the mutation in a gene or pathway described herein, and the second gRNA is used to target downstream (i.e., 3') of the mutation in a gene or pathway described herein). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Constructs/Components

The components, e.g., a Cas9 molecule or gRNA molecule, or both, can be delivered, formulated, or administered in a variety of forms. When a component is delivered encoded in DNA the DNA will typically include a control region, e.g., comprising a promoter, to effect expression. Useful promoters for Cas9 molecule sequences include CMV, EF-1a, MSCV, PGK, CAG control promoters. Useful promoters for sgRNAs include H1, EF-1a and U6 promoters. Promoters with similar or dissimilar strengths can be selected to tune the expression of components. Sequences encoding a Cas9 molecule can comprise a nuclear localization signal (NLS), e.g., an SV40 NLS. In an embodiment, a promoter for a Cas9 molecule or a sgRNA molecule can be, independently, inducible, tissue specific, or cell specific.

DNA-Based Delivery of a Cas9 Molecule and or a gRNA Molecule

DNA encoding Cas9 molecules (e.g., eaCas9 molecules or eiCas9 molecules) and/or gRNA molecules, can be administered to subjects or delivered into cells by art-known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof.

In some embodiments, the Cas9- and/or gRNA-encoding DNA is delivered by a vector (e.g., viral vector/virus or plasmid).

A vector can comprise a sequence that encodes a Cas9 molecule and/or a gRNA molecule. A vector can also comprise a sequence encoding a signal peptide (e.g., for nuclear localization, nucleolar localization, mitochondrial localization), fused, e.g., to a Cas9 molecule sequence. For example, a vector can comprise a nuclear localization sequence (e.g., from SV40) fused to the sequence encoding the Cas9 molecule.

One or more regulatory/control elements, e.g., a promoter, an enhancer, an intron, a polyadenylation signal, a Kozak consensus sequence, internal ribosome entry sites (IRES), a 2A sequence, and a splice acceptor or donor can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiments, the promoter is a constitutive promoter. In some embodiments, the promoter is a tissue specific promoter. In some embodiments, the promoter is a viral promoter. In other embodiments, the promoter is a non-viral promoter.

In some embodiments, the vector or delivery vehicle is a viral vector (e.g., for generation of recombinant viruses). In some embodiments, the virus is a DNA virus (e.g., dsDNA or ssDNA virus). In other embodiments, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses.

In some embodiments, the virus infects dividing cells. In other embodiments, the virus infects non-dividing cells. In some embodiments, the virus infects both dividing and non-dividing cells. In some embodiments, the virus can integrate into the host genome. In some embodiments, the virus is engineered to have reduced immunity, e.g., in human. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the Cas9 molecule and/or the gRNA molecule. In other embodiments, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In some embodiments, the Cas9- and/or gRNA-encoding DNA is delivered by a recombinant retrovirus. In some embodiments, the retrovirus (e.g., Moloney murine leukemia virus) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In some embodiments, the Cas9- and/or gRNA-encoding DNA is delivered by a recombinant lentivirus. For example, the lentivirus is replication-defective, e.g., does not comprise one or more genes required for viral replication.

In some embodiments, the Cas9- and/or gRNA-encoding DNA is delivered by a recombinant adenovirus. In some embodiments, the adenovirus is engineered to have reduced immunity in human.

In some embodiments, the Cas9- and/or gRNA-encoding DNA is delivered by a recombinant AAV. In some embodiments, the AAV can incorporate its genome into that of a host cell, e.g., a target cell as described herein. In some embodiments, the AAV is a self-complementary adeno-associated virus (scAAV), e.g., a scAAV that packages both strands which anneal together to form double stranded DNA. AAV serotypes that may be used in the disclosed methods include, e.g., AAV1, AAV2, modified AAV2 (e.g., modifications at Y444F, Y500F, Y730F and/or S662V), AAV3, modified AAV3 (e.g., modifications at Y705F, Y731 F and/or T492V), AAV4, AAV5, AAV6, modified AAV6 (e.g., modifications at S663V and/or T492V), AAV8, AAV 8.2, AAV9, AAV rh 10, and pseudotyped AAV, such as AAV2/8, AAV2/5 and AAV2/6 can also be used in the disclosed methods.

In some embodiments, the Cas9- and/or gRNA-encoding DNA is delivered by a hybrid virus, e.g., a hybrid of one or more of the viruses described herein.

A Packaging cell is used to form a virus particle that is capable of infecting a host or target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In an embodiment, the viral vector has the ability of cell type and/or tissue type recognition. For example, the viral vector can be pseudotyped with a different/alternative viral envelope glycoprotein; engineered with a cell type-specific receptor (e.g., geneticmodification of the viral envelope glycoproteins to incorporate targeting ligands such as a peptide ligand, a single chain antibodie, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemagglutin (HA) can be incorporated to increase viral uptake into cells. In an embodiment, the viral vector has the ability of nuclear localization. For example, a virus that requires the breakdown of the cell wall (during cell division) and therefore will not infect a non-diving cell can be altered to incorporate a nuclear localization peptide in the matrix protein of the virus thereby enabling the transduction of non-proliferating cells.

In some embodiments, the Cas9- and/or gRNA-encoding DNA is delivered by a non-vector based method (e.g., using naked DNA or DNA complexes). For example, the DNA can be delivered, e.g., by organically modified silica or silicate (Ormosil), electroporation, gene gun, sonoporation, magnetofection, lipid-mediated transfection, dendrimers, inorganic nanoparticles, calcium phosphates, or a combination thereof.

In some embodiments, the Cas9- and/or gRNA-encoding DNA is delivered by a combination of a vector and a non-vector based method. For example, a virosome comprises a liposome combined with an inactivated virus (e.g., HIV or influenza virus), which can result in more efficient gene transfer, e.g., in a respiratory epithelial cell than either a viral or a liposomal method alone.

In an embodiment, the delivery vehicle is a non-viral vector. In an embodiment, the non-viral vector is an inorganic nanoparticle (e.g., attached to the payload to the surface of the nanoparticle). Exemplary inorganic nanoparticles include, e.g., magnetic nanoparticles (e.g., $Fe_3MnO_2$), or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

In an embodiment, the vehicle has targeting modifications to increase target cell update of nanoparticles and liposomes, e.g., cell specific antigens, monoclonal antibodies, single chain antibodies, aptamers, polymers, sugars, and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands). In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovescicle (30-100 nm) of endocytic origin (e.g., can be produced from various cell types and can therefore be taken up by cells without the need of for targeting ligands).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNA Encoding a Cas9 Molecule

RNA encoding Cas9 molecules (e.g., eaCas9 molecules, eiCas9 molecules or eiCas9 fusion proteins) and/or gRNA molecules, can be delivered into cells, e.g., target cells described herein, by art-known methods or as, described herein. For example, Cas9-encoding and/or gRNA-encoding RNA can be delivered, e.g., by microinjection, electroporation, lipid-mediated transfection, peptide-mediated delivery, or a combination thereof.

Route of Administration

Systemic modes of administration include oral and parenteral routes. Parenteral routes include, by way of aerosol, intravenous, intrarterial, intraosseous, intramuscular, intradermal, subcutaneous, intranasal and intraperitoneal routes.

Example 1

Personalized Molecular Surgical Therapy of EGFR Mutations

We recently published a report describing CRISPR/Cas-mediated genome editing to treat EGFR-mutant lung cancer (Tang, H. and Shraer, J. B. 2016 *EMBO Molecular Medicine* 8: 83-85). While substantial progress has been made in the treatment of lung cancer with the development of tyrosine kinase inhibitors (TKIs) that target tumor-driving mutations in the epidermal growth factor receptor (EGFR), nearly all patients treated with TKIs ultimately develop drug resistance due to resistance-conferring genomic mutations. CRISPR/Cas9-mediated genome editing is a powerful new technique that allows precise changes to be made to cells' genomes. This technology is currently used widely in research laboratories, but it has yet to make an impact in the clinics. We have developed a clinical application for this technical advance, allowing personalized, molecular surgery to correct or destroy mutated EGFR. After detection of EGFR mutations in individual patients' cancers from biopsy samples, the EGFR-mutant genes are repaired or destroyed with virus-delivered CRISPR/Cas system. We demonstrate the feasibility of such an approach with examples from the most common primary and secondary EGFR mutations that are encountered. These "molecular surgeries" on genomic DNA directly target the cause of the disease in a personalized manner. This approach may be combined with traditional surgery, radiation therapy, or chemo/targeted therapy.

Figure 4:
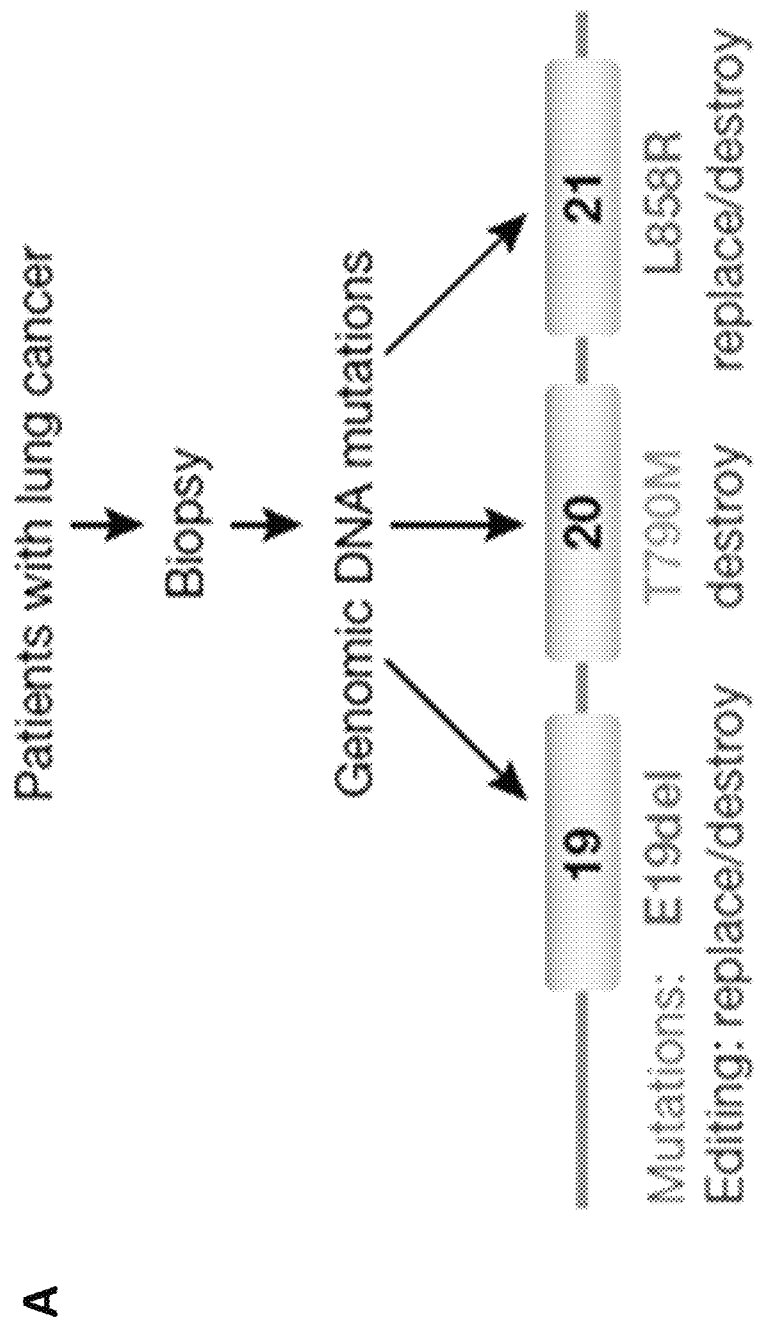
FIG. 4. Strategy for personalized molecular surgical therapy to treat EGFR-mutant lung cancer with CRISPR/Cas9 technology. (A) Tumor tissue obtained by biopsy from a lung cancer patient. Genomic mutations in the EGFR gene will be identified by PCR and sequencing. The common mutations are shown, but rare mutations could be addressed as well. (B) Correction of the mutated EGFR gene by homology-directed repair (HDR), substituting the mutated sequence with wild-type sequence. Examples from exons 19 and 21 are shown. Nickase is used to create single-strand nicks on genomic DNA. (C) Destruction of the mutated EGFR gene through HDR or NHEJ-mediated truncation, insertion, and deletion. Potential sgRNA targeting sequences against exon 20 T790M (point mutation shown; SEQ ID NO: 21) and exon 19 deletion (del EFREA; SEQ ID NO: 4) are shown in italics. The PAM sequence (NGG) is shown, and the deleted 15-bp sequence formerly sat between the nucleotides labeled with gray and black fonts. HDR-mediated introduction of a sequence with a stop codon will yield a truncated EGFR protein lacking tyrosine kinase activity. Similarly, NHEJ would introduce a random indel leading to truncation, deletion, and/or insertion that cause destruction of tyrosine kinase activity. (D) Virus-mediated delivery of the CRISPR/Cas9 system. In some embodiments, CRISPR/Cas9 DNA constructs are packaged into vims and delivered to patients via the trachea for localized cancers, or intravascularly for metastatic cancers.
Figure 4:
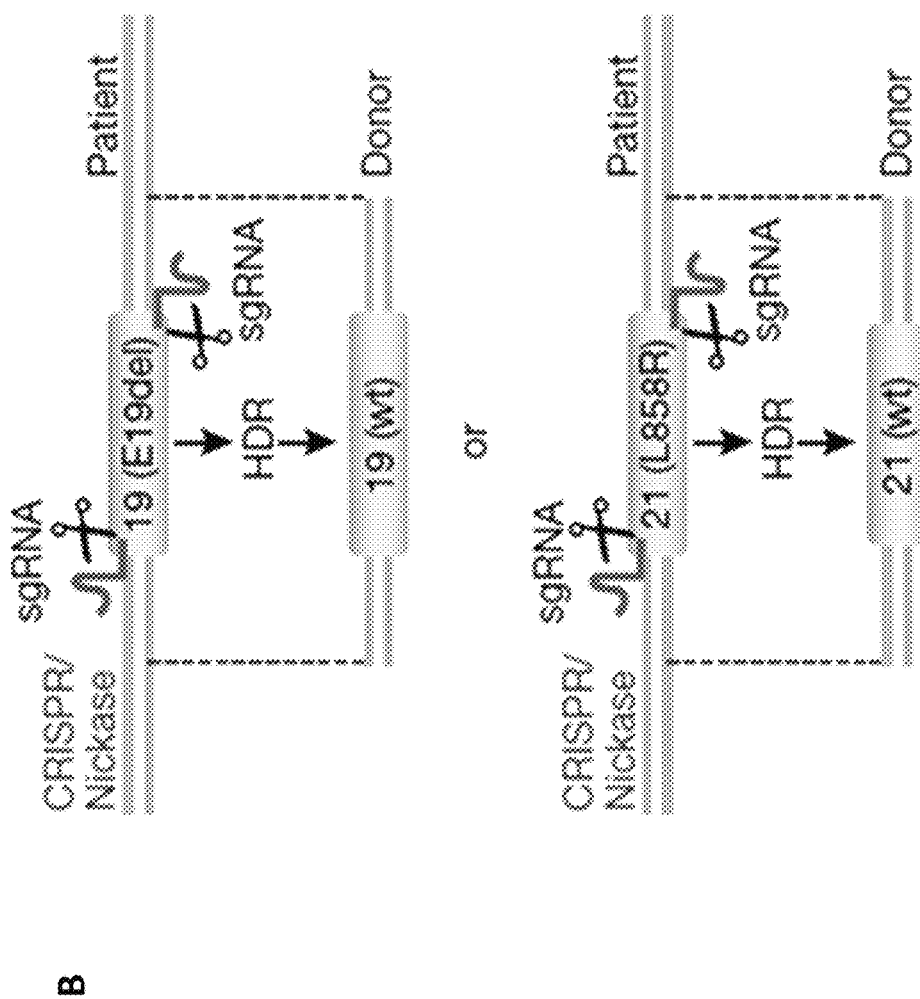
Figure 4:
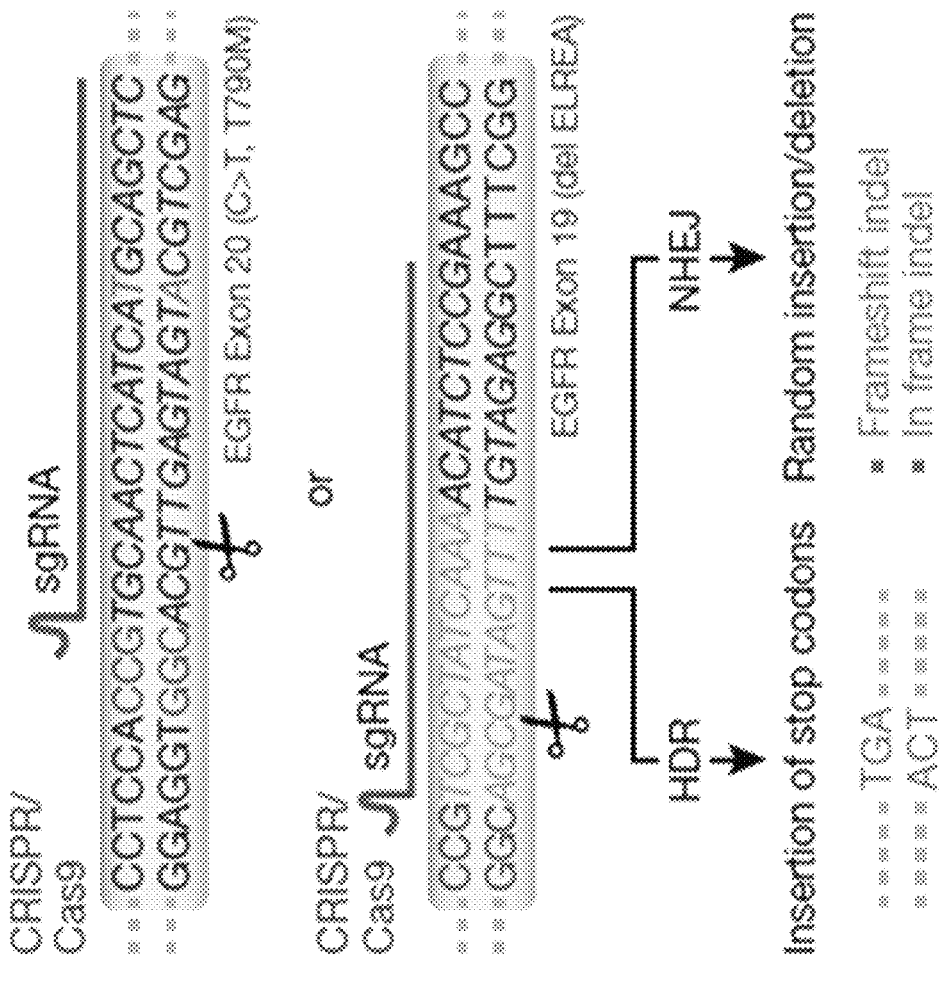
Figure 4:
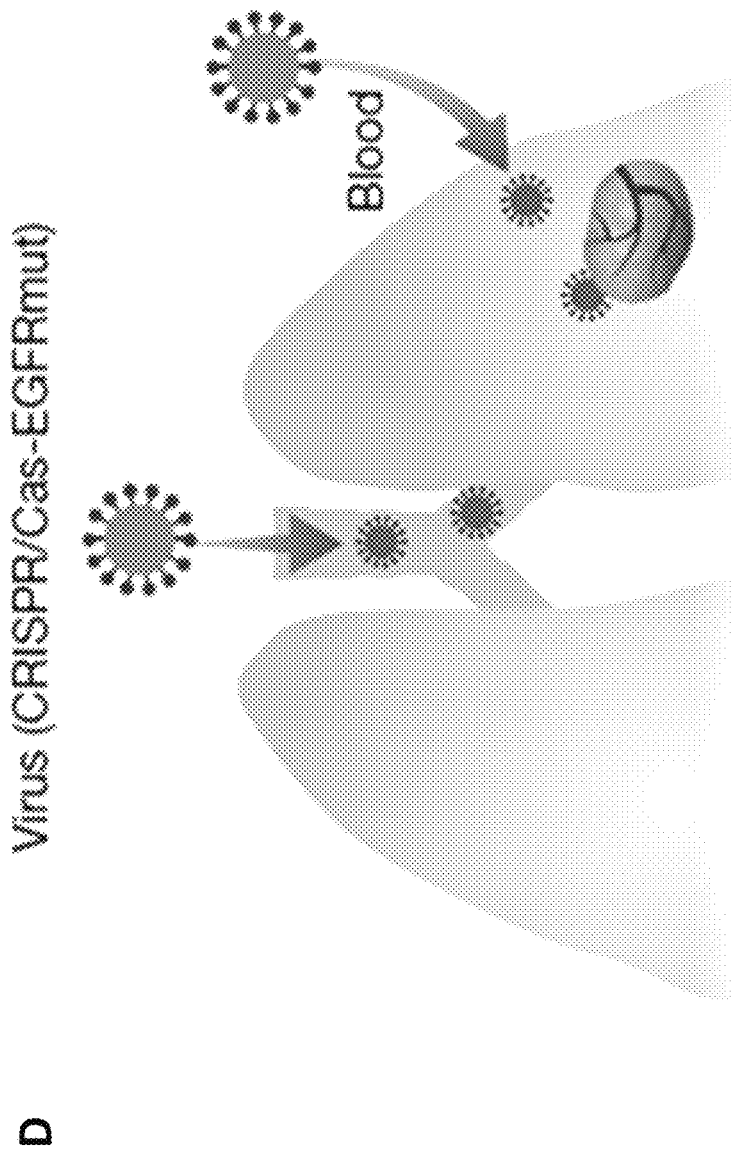

This type of molecular surgery for lung cancer utilizes CRISPR/Cas9 to repair or destroy the EGFR gene in EGFR-mutant NSCLC, as shown in FIG. 4, A, with examples from the most common primary and secondary mutations. First, biopsy samples from patients are tested for the mutations. sgRNA is designed (FIGS. 4, B and C) to target the specific sequences in the mutated exons—for example, L858R in exon 21, E19del in exon 19, or the T790M resistance mutation in exon 20 (FIG. 4, A). To repair the mutated EGFR, we utilize CRISPR/Cas9 nickase to target the DNA sequences flanking the mutation (or the whole exon if there are additional mutations in the exon). Briefly, CRISPR/Cas9 nickase creates single-strand breaks in the genomic DNA sequence on each side of the mutations or exons (e.g., exon 19 or 21). The donor DNA harboring the wild-type sequence of exon 19 or 21 and its right and left homologous arms replace the mutated sequence or exon via homologous recombination (i.e., HDR) (FIG. 4, B). This replacement eradicates the carcinogenic mutations, ends the constitutively activated TK activity, and thereby prevents cancer progression. This type of approach is of great benefit in primary EGFR mutations (e.g., E19del, L858R), or when there are multiple mutations in same exon (FIG. 4, B).

To destroy the mutated EGFR, we utilize CRISPR/Cas9 to target the mutated DNA sequence in the EGFR's tyrosine kinase domain and introduce a stop codon (HDR) or indel (NHEJ) to interrupt EGFR protein translation. The altered EGFR protein is non-functional and therefore loses its oncogenic activity. This mutation-directed destruction is applied to any mutation or deletion in the tyrosine kinase domain (from exons 18 to 24), including the more common mutations, as long as an appropriate mutation-targeting sgRNA is available. We show in FIG. 4, C potential mutation recognition sgRNA sequences designed to target the sequences at the exon 20 T790M and the exon 19 del. CRISPR/Cas9-mediated editing leads to HDR-dependent insertion of a stop codon that terminates EGFR translation at exon 19 or 20, or an NHEJ-dependent random insertion/deletion, destroying EGFR TK activity and cancer progression.

CRISPR/Cas9 systems (gRNA and Cas9 expression plasmid, donor DNA plasmid) can be packaged into viruses and are delivered to patients intratracheally (for treatment of localized cancer), or intravascularly (for metastatic cancer) (FIG. 4, D).

These "molecular surgeries" on genomic DNA in EGFR-mutant lung cancer directly target the cause of the disease in a personalized manner. A similar strategy is employed to target other types of cancer-driving genomic changes, such as the rearranged anaplastic lymphoma kinase (ALK) allele and K-ras mutations. This approach provide an alternative form of therapy that avert the need for costly, lengthy, and apparently endless process of developing new TKIs against new mutations. As with any therapy, this strategy may subverted by feedback disinhibition of other cellular proliferation pathways. However, at a minimum, CRISPR/Cas therapy prevents secondary genomic mutations that are the main cause of TKI resistance. Well-designed sgRNAs, careful management of the potential off-target effects, and efficient delivery are necessary for the success of CRISPR/Cas-mediated therapy. Combining this molecular surgical approach with traditional surgery, radiation, and/or TKI treatment has the potential to significantly improve the survival of patients with EGFR-mutant non-small cell lung cancer (NSCLC).

Design of sgRNAs

Targeting Exon 19 Deletion (A) Genomic DNA sequence in EGFR's Exon 19 with deletion mutation:

```
                                              (SEQ ID NO: 2)
ATTCCCGTCGCTATCAAA ACATCTCCGAAAGCCAACAAAGAA
```

The deletion deletes 15 nucleotides, which are missing between the underlined and the bold sequences.

(B) Coding DNA sequence and corresponding RNA sequence of sgRNA that can target Exon19 of EGFR with deletion—PAM NGG

```
        DelG1:
                                              (SEQ ID NO: 3)
              (DNA) CGGAGATGTTTTGATAGCGA (SEQ ID NO: 4)
              (RNA) CGGAGAUGUUUUGAUAGCGA
```

```
DelG2:
                                            (SEQ ID NO: 5)
       (DNA)  GGAGATGTTTTGATAGCGAC (SEQ ID NO: 6)
       (RNA)  GGAGAUGUUUUGAUAGCGAC
```

(C) Coding DNA sequence and corresponding RNA sequence of sgRNA that can target Exon19 of EGFR with deletion—PAM NGA

```
DelG3:
                                            (SEQ ID NO: 7)
       (DNA)  CGTCGCTATCAAAACATCTC (SEQ ID NO: 8)
       (RNA)  CGUCGCUAUCAAAACAUCUC

DelG4:
                                            (SEQ ID NO: 9)
       (DNA)  GAGATGTTTTGATAGCGACG (SEQ ID NO: 10)
       (RNA)  GAGAUGUUUUGAUAGCGACG

DelG5:
                                            (SEQ ID NO: 11)
       (DNA)  TTTCGGAGATGTTTTGATAG (SEQ ID NO: 12)
       (RNA)  UUUCGGAGAUGUUUUGAUAG

DelG6:
                                            (SEQ ID NO: 13)
       (DNA)  GTTGGCTTTCGGAGATGTTT (SEQ ID NO: 14)
       (RNA)  GUUGGCUUUCGGAGAUGUUU
```

Targeting Exon 20 of EGFR, T790M Drug Resistant Mutation (A) Genomic DNA sequence in EGFR's Exon 20 with point mutation (T790M):

```
                                            (SEQ ID NO: 15)
ACCTCCACCGTGCAACTCATCATGCAGCTCATGCCCTTCGGCTGCCTCCT
```

Here, C is mutated into T, changing threonine 790 to methionine, i.e., T790M.

(B) Coding DNA sequence and corresponding RNA sequence of sgRNA that can target Exon20 T790M point mutation—PAM NGG

```
ptG1:
                                            (SEQ ID NO: 16)
       (DNA)  CTGCATGATGAGTTGCACGG (SEQ ID NO: 17)
       (RNA)  CUGCAUGAUGAGUUGCACGG ptG2:
                                            (SEQ ID NO: 18)
       (DNA)  CATGATGAGTTGCACGGTGG (SEQ ID NO: 19)
       (RNA)  CAUGAUGAGUUGCACGGUGG ptG3:
                                            (SEQ ID NO: 20)
       (DNA)  GAGCTGCATGATGAGTTGCA (SEQ ID NO: 21)
       (RNA)  GAGCUGCAUGAUGAGUUGCA
```

(C) Coding DNA sequence and corresponding RNA sequence of sgRNA that can target Exon20 T790M point mutation—PAM NGA

```
ptG4:
                                            (SEQ ID NO: 22)
       (DNA)  GCCGAAGGGCATGAGCTGCA (SEQ ID NO: 23)
       (RNA)  GCCGAAGGGCAUGAGCUGCA ptG5:
                                            (SEQ ID NO: 24)
       (DNA)  GAAGGGCATGAGCTGCATGA (SEQ ID NO: 25)
       (RNA)  GAAGGGCAUGAGCUGCAUGA
```

Targeting Exon 21 (L858R Mutation)

A) Genomic DNA sequence in EGFR's Exon 21 with point mutation (L858R):

```
                                            (SEQ ID NO: 26)
AAACACCGCAGCATGTCAAGATCACAGATTTTGGGCGGGCCAAACTGCTG

GGTGCGGAAG
```

Here, T is mutated into G, changing leucine858 to arginine, i.e., L858R.

B) Coding DNA sequence and corresponding RNA sequence of sgRNA that can target Exon21 L858R point mutation—PAM NGG

```
L858RG1:
                                            (SEQ ID NO: 27)
       (DNA)  CAAGATCACAGATTTTGGGC (SEQ ID NO: 28)
       (RNA)  CAAGAUCACAGAUUUUGGGC

L858RG2:
                                            (SEQ ID NO: 29)
       (DNA)  TCAAGATCACAGATTTTGGG (SEQ ID NO: 30)
       (RNA)  UCAAGAUCACAGAUUUUGGG

L858RG3:
                                            (SEQ ID NO: 31)
       (DNA)  TTTTGGGCGGGCCAAACTGC (SEQ ID NO: 32)
       (RNA)  UUUUGGGCGGGCCAAACUGC

L858RG4:
                                            (SEQ ID NO: 33)
       (DNA)  TTTGGGCGGGCCAAACTGCT (SEQ ID NO: 34)
       (RNA)  UUUGGGCGGGCCAAACUGCU

L858RG5:
                                            (SEQ ID NO: 35)
       (DNA)  GCGGGCCAAACTGCTGGGTG (SEQ ID NO: 36)
       (RNA)  GCGGGCCAAACUGCUGGGUG
```

C) Coding DNA sequence and corresponding RNA sequence of sgRNA that can target Exon21 of L858R point mutation—PAM NGA

```
L858RG6:
                                   (SEQ ID NO: 37)
(DNA)  TTTGGCCCGCCCAAAATCTG (SEQ ID NO: 38)
(RNA)  UUUGGCCCGCCCAAAAUCUG

L858RG7:
                                   (SEQ ID NO: 39)
(DNA)  CCGCCCAAAATCTGTGATCT (SEQ ID NO: 40)
(RNA)  CCGCCCAAAAUCUGUGAUCU
```

Cells Used

H1299: human lung cancer cells, with wildtype (no mutation) EGFR.

H1975: human lung cancer cells, with T790M mutation on Exon 20 and L858R mutation on Exon 21;

H1650: human lung cancer cells, with Exon 19 deletion mutation

Experimental Results

Figure 5:
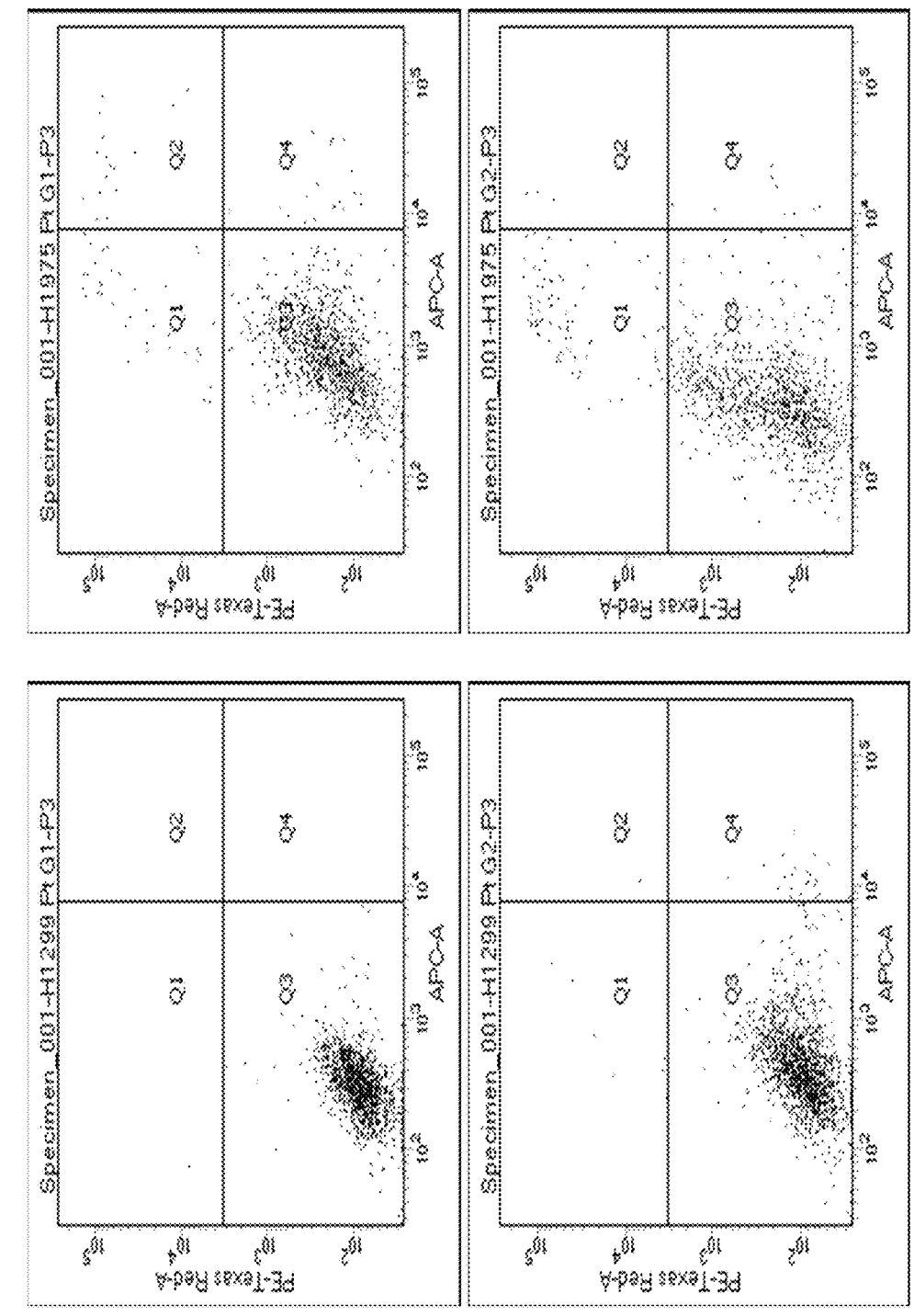
FIG. 5. Cultured H1299 and H1975 cells were transfected with sgRNAs (ptG1 and ptG2) that target surrounding sequence of T790M in exon20 of EGFR for 2 days and subjected to apoptotic analysis. (A) Flow cytometry after staining the transfected cells. (B) Quantitative data of the apoptotic population in transfected cells.
Figure 5:
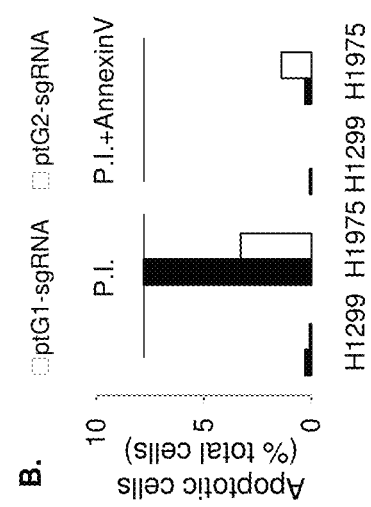

Referring to FIG. 5, cultured H1299 and H1975 cells were transfected with sgRNAs (ptG1 and ptG2) that target surrounding sequence of T790M in exon20 of EGFR for 2 days and were subjected to apoptotic analysis. In FIG. 5, A, flow cytometry after staining the transfected cells demonstrates that ptG1 and ptG2 induce apoptosis in H1975 cells, but not in H1299 cells. This indicates that both the ptG1 and ptG2 sgRNAs specifically target the mutated sequence, but not the non-mutated sequence. FIG. 5, B shows quantitative data of the apoptotic population in transfected cells.

Example 2

Reporter System for Screening for Effective gRNAs

Figure 6:
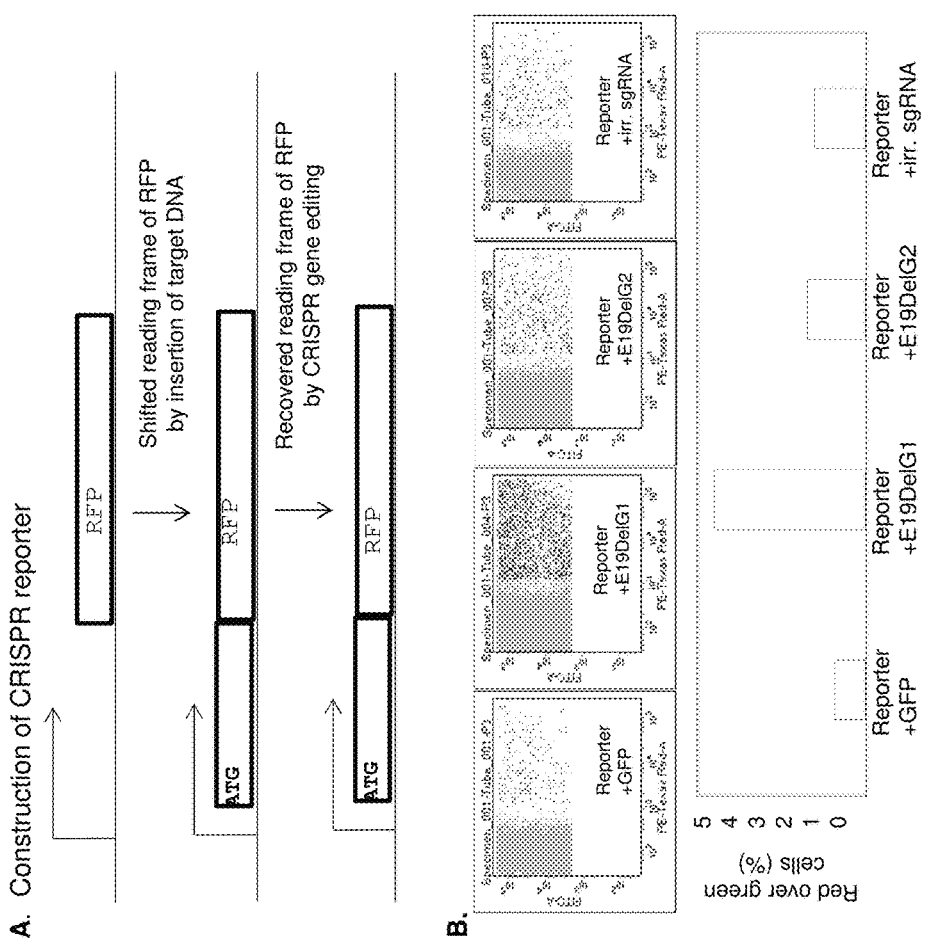
FIG. 6. Screen for effective sgRNAs against a target sequence in EGFR. (A) A reporter system for screening effective sgRNAs. (B) E19DelG1 is an efficient sgRNA targeting the surrounding sequence of exon 19 deletion mutation, shown by the reporter system.

We constructed a CRISPR reporter gene construct, which provides a rapid way to screen for a gRNA-mediated shift in reading frame or for a gRNA-mediated restoration of a reading frame. The reporter gene construct is a target template for editing by CRISPR/Cas gene editing. The reporter construct encodes a fusion protein comprising an EGFR amino acid sequence linked in-frame to red fluorescent protein (RFP). Referring to FIG. 6, A, insertion of a sequence, e.g., resulting in a fame shift or to include a stop codon, results in the expression of nonfunctional RFP. Conversely, repair of a mutant EGFR sequence can recover the reading frame of the fusion protein, resulting in expression of functional RFP. In FIG. 6, B, the reporter system demonstrates recovery of the reading frame of RFP following CRISPR gene editing using the DelG1 guide RNA.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with accompanying drawings. However, it should be understood that the figures are not drawn to scale. Components can be added, removed, and/or rearranged. Further, the disclosure herein of any particular feature, aspect, method, property, characteristic, quality, attribute, element, or the like in connection with various embodiments can be used in all other embodiments set forth herein.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

INCORPORATION BY REFERENCE

All publications, patents, and patent applications mentioned herein are hereby incorporated by reference in their entirety as if each individual publication, patent or patent application was specifically and individually indicated to be incorporated by reference.

What is claimed is:

1. A clustered regularly interspaced short palindromic repeats (CRISPR)/Cas guide RNA (gRNA) comprising a targeting domain that is complementary to human genomic Epidermal Growth Factor Receptor (EGFR) DNA, wherein the targeting domain is configured to:

(a) restore or destroy a wild type sequence at E746-A750 in exon 19, (b) restore or destroy a threonine residue at position 790 in exon 20, or (c) restore or destroy a leucine at position 858 in exon 21.

2. The gRNA according to claim 1, further comprising:

a first complementarity domain;

a linking domain;

a second complementarity domain, which is complementary to the first complementarity domain;

a proximal domain; and optionally, a tail domain.

3. The gRNA according to claim 1 comprising a sequence selected from the group consisting of SEQ ID NO: 4, SEQ ID NO: 6, SEQ ID NO: 8, SEQ ID NO: 10, SEQ ID NO: 12 and SEQ ID NO: 14.

4. The gRNA according to claim 1 comprising a sequence selected from the group consisting of SEQ ID NO: 17, SEQ ID NO: 19, SEQ ID NO: 21, SEQ ID NO: 23, and SEQ ID NO: 25.

5. The gRNA according to claim 1 comprising a sequence selected from the group consisting of SEQ ID NO: 28, SEQ ID NO: 30, SEQ ID NO: 32, SEQ ID NO: 34, SEQ ID NO: 36, SEQ ID NO: 38 and SEQ ID NO: 40.

6. A vector system comprising one or more packaged vector(s) comprising:
   (a) a first regulatory element operably linked to a sequence encoding a gRNA according to claim 1, and
   (b) a second regulatory element operably linked to a nucleic acid encoding a Cas protein.

7. The vector system according to claim 6, wherein the Cas protein is a Cas9 protein.

8. The vector system according to claim 7, wherein the Cas9 protein is selected from the group consisting of *Streptococcus pyogenes* Cas9, *Streptococcus thermophilus* Cas9, *Staphylococcus aureus* Cas9 and *Neisseria meningitides* Cas9.

9. The vector system according to claim 6, wherein said one or more packaged vectors is/are selected from the group consisting of retroviruses, lentiviruses, adenovirus, adeno-associated virus (AAV), vaccinia viruses, poxviruses, and herpes simplex viruses.

10. The vector system according to claim 6 comprising only a single packaged vector.

11. A method of altering a nucleic acid sequence encoding EGFR in a cell comprising contacting said cell with a vector system according to claim 6.

12. A method of treating lung cancer in a subject comprising administering a vector system according to claim 6 to said subject.

13. The method according to claim 12, wherein said lung cancer is a non-small cell lung cancer (NSCLC).

14. A method of selectively inducing apoptosis in a cell comprising administering a gRNA according to claim 1 to said cell.

* * * * *

SEQUENCE LISTING

```
<160> NUMBER OF SEQ ID NOS: 40

<210> SEQ ID NO 1
<211> LENGTH: 1210
<212> TYPE: PRT
<213> ORGANISM: Homo sapiens
```

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
```

```
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
            645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
            725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
            805                 810                 815
Trp Cys Val Gln Ile Ala Lys Gly Met Asn Tyr Leu Glu Asp Arg Arg
            820                 825                 830
```

```
Leu Val His Arg Asp Leu Ala Ala Arg Asn Val Leu Lys Thr Pro
        835                 840                 845

Gln His Val Lys Ile Thr Asp Phe Gly Leu Ala Lys Leu Leu Gly Ala
        850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210

<210> SEQ ID NO 2
<211> LENGTH: 42
```

```
<212> TYPE: DNA
<213> ORGANISM: Homo sapiens

<400> SEQUENCE: 2
attcccgtcg ctatcaaaac atctccgaaa gccaacaaag aa                              42

<210> SEQ ID NO 3
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 3
cggagatgtt ttgatagcga                                                       20

<210> SEQ ID NO 4
<211> LENGTH: 20
<212> TYPE: RNA
<213> ORGANISM: Artificial Sequence
<220> FEATURE:
<223> OTHER INFORMATION: gRNA

<400> SEQUENCE: 4
cggagauguu uugauagcga                                                       20

<210> SEQ ID NO 5
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 5
ggagatgttt tgatagcgac                                                       20

<210> SEQ ID NO 6
<211> LENGTH: 20
<212> TYPE: RNA
<213> ORGANISM: Artificial Sequence
<220> FEATURE:
<223> OTHER INFORMATION: gRNA

<400> SEQUENCE: 6
ggagauguuu ugauagcgac                                                       20

<210> SEQ ID NO 7
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 7
cgtcgctatc aaaacatctc                                                       20

<210> SEQ ID NO 8
<211> LENGTH: 20
<212> TYPE: RNA
<213> ORGANISM: Artificial Sequence
<220> FEATURE:
<223> OTHER INFORMATION: gRNA

<400> SEQUENCE: 8
cgucgcuauc aaaacaucuc                                                       20
```

```
<210> SEQ ID NO 9
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 9
gagatgtttt gatagcgacg                                               20

<210> SEQ ID NO 10
<211> LENGTH: 20
<212> TYPE: RNA
<213> ORGANISM: Artificial Sequence
<220> FEATURE:
<223> OTHER INFORMATION: gRNA

<400> SEQUENCE: 10
gagauguuuu gauagcgacg                                               20

<210> SEQ ID NO 11
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 11
tttcggagat gttttgatag                                               20

<210> SEQ ID NO 12
<211> LENGTH: 20
<212> TYPE: RNA
<213> ORGANISM: Artificial Sequence
<220> FEATURE:
<223> OTHER INFORMATION: gRNA

<400> SEQUENCE: 12
uuucggagau guuuugauag                                               20

<210> SEQ ID NO 13
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 13
gttggctttc ggagatgttt                                               20

<210> SEQ ID NO 14
<211> LENGTH: 20
<212> TYPE: RNA
<213> ORGANISM: Artificial Sequence
<220> FEATURE:
<223> OTHER INFORMATION: gRNA

<400> SEQUENCE: 14
guuggcuuuc ggagauguuu                                               20

<210> SEQ ID NO 15
<211> LENGTH: 50
<212> TYPE: DNA
<213> ORGANISM: Homo sapiens

<400> SEQUENCE: 15
```
acctccaccg tgcaactcat catgcagctc atgcccttcg gctgcctcct    50

```
<210> SEQ ID NO 16
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 16
```
ctgcatgatg agttgcacgg    20

```
<210> SEQ ID NO 17
<211> LENGTH: 20
<212> TYPE: RNA
<213> ORGANISM: Artificial Sequence
<220> FEATURE:
<223> OTHER INFORMATION: gRNA

<400> SEQUENCE: 17
```
cugcaugaug aguugcacgg    20

```
<210> SEQ ID NO 18
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 18
```
catgatgagt tgcacggtgg    20

```
<210> SEQ ID NO 19
<211> LENGTH: 20
<212> TYPE: RNA
<213> ORGANISM: Artificial Sequence
<220> FEATURE:
<223> OTHER INFORMATION: gRNA

<400> SEQUENCE: 19
```
caugaugagu ugcacggugg    20

```
<210> SEQ ID NO 20
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 20
```
gagctgcatg atgagttgca    20

```
<210> SEQ ID NO 21
<211> LENGTH: 20
<212> TYPE: RNA
<213> ORGANISM: Artificial Sequence
<220> FEATURE:
<223> OTHER INFORMATION: gRNA

<400> SEQUENCE: 21
```
gagcugcaug augaguugca    20

```
<210> SEQ ID NO 22
<211> LENGTH: 20
<212> TYPE: DNA
```

```
<213> ORGANISM: Artificial Sequence
<220> FEATURE:
<223> OTHER INFORMATION: sequence encoding gRNA

<400> SEQUENCE: 22
gccgaagggc atgagctgca                                              20

<210> SEQ ID NO 23
<211> LENGTH: 20
<212> TYPE: RNA
<213> ORGANISM: Artificial Sequence
<220> FEATURE:
<223> OTHER INFORMATION: gRNA

<400> SEQUENCE: 23
gccgaagggc augagcugca                                              20

<210> SEQ ID NO 24
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 24
gaagggcatg agctgcatga                                              20

<210> SEQ ID NO 25
<211> LENGTH: 20
<212> TYPE: RNA
<213> ORGANISM: Artificial Sequence
<220> FEATURE:
<223> OTHER INFORMATION: gRNA

<400> SEQUENCE: 25
gaagggcaug agcugcauga                                              20

<210> SEQ ID NO 26
<211> LENGTH: 60
<212> TYPE: DNA
<213> ORGANISM: Homo sapiens

<400> SEQUENCE: 26
aaacaccgca gcatgtcaag atcacagatt ttgggcgggc caaactgctg ggtgcggaag    60

<210> SEQ ID NO 27
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 27
caagatcaca gattttgggc                                              20

<210> SEQ ID NO 28
<211> LENGTH: 20
<212> TYPE: RNA
<213> ORGANISM: Artificial Sequence
<220> FEATURE:
<223> OTHER INFORMATION: gRNA

<400> SEQUENCE: 28
caagaucaca gauuugggc                                               20
```

```
<210> SEQ ID NO 29
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 29
tcaagatcac agattttggg                                              20

<210> SEQ ID NO 30
<211> LENGTH: 20
<212> TYPE: RNA
<213> ORGANISM: Artificial Sequence
<220> FEATURE:
<223> OTHER INFORMATION: gRNA

<400> SEQUENCE: 30
ucaagaucac agauuuuggg                                              20

<210> SEQ ID NO 31
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 31
ttttgggcgg gccaaactgc                                              20

<210> SEQ ID NO 32
<211> LENGTH: 20
<212> TYPE: RNA
<213> ORGANISM: Artificial Sequence
<220> FEATURE:
<223> OTHER INFORMATION: gRNA

<400> SEQUENCE: 32
uuuugggcgg gccaaacugc                                              20

<210> SEQ ID NO 33
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 33
tttgggcggg ccaaactgct                                              20

<210> SEQ ID NO 34
<211> LENGTH: 20
<212> TYPE: RNA
<213> ORGANISM: Artificial Sequence
<220> FEATURE:
<223> OTHER INFORMATION: gRNA

<400> SEQUENCE: 34
uuugggcggg ccaaacugcu                                              20

<210> SEQ ID NO 35
<211> LENGTH: 20
<212> TYPE: DNA
<213> ORGANISM: Artificial Sequence
<220> FEATURE:
<223> OTHER INFORMATION: sequence encoding gRNA
```

-continued

```
<400> SEQUENCE: 35
gcgggccaaa ctgctgggtg                                              20

<210> SEQ ID NO 36
<211> LENGTH: 20
<212> TYPE: RNA
<213> ORGANISM: Artificial Sequence
<220> FEATURE:
<223> OTHER INFORMATION: gRNA

<400> SEQUENCE: 36
gcgggccaaa cugcugggug                                              20

<210> SEQ ID NO 37
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 37
tttggcccgc ccaaaatctg                                              20

<210> SEQ ID NO 38
<211> LENGTH: 20
<212> TYPE: RNA
<213> ORGANISM: Artificial Sequence
<220> FEATURE:
<223> OTHER INFORMATION: gRNA

<400> SEQUENCE: 38
uuuggcccgc ccaaaaucug                                              20

<210> SEQ ID NO 39
<211> LENGTH: 20
<212> TYPE: DNA
<213> ORGANISM: Artificial Sequence
<220> FEATURE:
<223> OTHER INFORMATION: sequence encoding gRNA

<400> SEQUENCE: 39
ccgcccaaaa tctgtgatct                                              20

<210> SEQ ID NO 40
<211> LENGTH: 20
<212> TYPE: RNA
<213> ORGANISM: Artificial Sequence
<220> FEATURE:
<223> OTHER INFORMATION: gRNA

<400> SEQUENCE: 40
ccgcccaaaa ucugugaucu                                              20
```

UNITED STATES PATENT AND TRADEMARK OFFICE
CERTIFICATE OF CORRECTION

| | |
|---|---|
| PATENT NO. | : 10,240,145 B2 |
| APPLICATION NO. | : 15/360627 |
| DATED | : March 26, 2019 |
| INVENTOR(S) | : Huibin Tang |

It is certified that error appears in the above-identified patent and that said Letters Patent is hereby corrected as shown below:

In the Specification

In Column 4, Line 13, after "NO: 1)" insert --.--.

In Column 4, Line 30, change "EFREA;" to --ELREA;--.

In Column 4, Line 40, change "vims" to --virus--.

In Column 10, Line 6, change "wildype," to --wildtype,--.

In Column 10, Line 8, change "the a" to --a--.

In Column 19, Line 21, change "and or" to --and/or--.

In Column 21, Line 18, change "antibodie," to --antibody,--.

In Column 21, Line 32, change "hemagglutin" to --hemagglutinin--.

In Column 22, Line 42, change "nanovescicle" to --nanovesicle--.

In Column 23, Line 17, change "intrarterial," to --intraarterial,--.

In Column 27, Line 20 (Approx.), after "mutation" insert --.--.

Signed and Sealed this
First Day of October, 2019

Andrei Iancu
*Director of the United States Patent and Trademark Office*